United States Patent [19]

Ledochowski et al.

[11] 4,150,231
[45] Apr. 17, 1979

[54] 1-NITRO-9-DIALKYLAMINOISOALK-YLAMINOACRIDINES OR THEIR SALTS

[75] Inventors: Andrzej Ledóchowski, Gdańsk-Oliwa; Jerzy Giełdanowski; Czesław Radzikowski, both of Wrocław; Cecylia Kwaśniewska-Rokicinska, Gliwice; Barbara Wysocka-Skrzela, Gdańsk; Lucyna Sawińska, Warsaw; Mieczysław Medon, Jelenia Góra, all of Poland

[73] Assignee: Politechnika Gdanska, Gdańsk-Wrzeszoz, Poland

[21] Appl. No.: 781,492

[22] Filed: Mar. 25, 1977

[30] Foreign Application Priority Data

Apr. 6, 1976 [PL] Poland ............................ 188528

[51] Int. Cl.² .................... C07D 219/12; A61K 31/47
[52] U.S. Cl. ..................................... 546/106; 424/257
[58] Field of Search ........................... 260/279 A

[56] References Cited

U.S. PATENT DOCUMENTS 1,962,277   6/1934   Jensch et al. ..................... 260/279 A

FOREIGN PATENT DOCUMENTS

1093847 12/1967 United Kingdom .................... 546/106

OTHER PUBLICATIONS

Konopa et al, Chem. Abstracts, v. 71, 37,302s (1969).
Ledochowski, Chem. Abstracts, v. 67, 64,226u (1967).

*Primary Examiner*—Donald G. Daus
*Assistant Examiner*—Diana G. Rivers
*Attorney, Agent, or Firm*—Haseltine, Lake & Waters

[57] ABSTRACT

1-Nitro-9-dialkylaminoisoalkylaminoacridines or their salts of the formula:

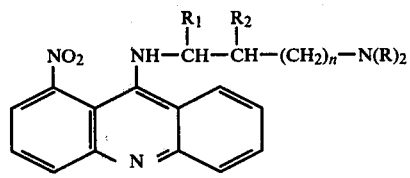

wherein R is lower alkyl, such as methyl, ethyl, $R^1$ is a hydrogen atom or methyl, $R^2$ is the same as $R^1$, with the proviso that $R^1$ is not equal to $R^2$ and $n = 0$ or 2, and their preparation is described. These compounds are useful as anti-neoplastic agents.

2 Claims, No Drawings

1-NITRO-9-DIALKYLAMINOISOALKYLAMINOACRIDINES OR THEIR SALTS

The subject of the present invention are the 1-nitro-9-dialkylaminoisoalkylaminoacridines, or their salts, of the formula 1:

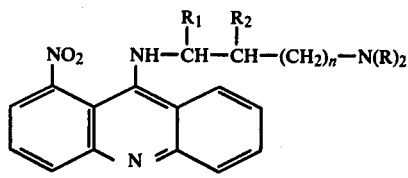

wherein R is lower alkyl, such as methyl and ethyl, $R^1$ is a hydrogen atom or methyl, $R^2$ is the same as $R^1$, with the proviso that $R^1$ is not equal to $R^2$, and n = 0 or 2, as well as to a method for preparing these compounds.

To date, from British Pat. No. 1,093,847 are known the 1-nitro-9-dialkylaminoalkylaminoacridines with normal alkyl chains, which are obtained by condensation of 1-nitro-9-chloroacridine, melting point, 150°–151° C., with dialkylaminoalkylamine. The reaction is carried out in an organic solvent medium, such as phenol or cresol, at a temperature of from 20° to 100° C., and the resulting product is isolated from the reaction medium by known methods.

A disadvantage of the compounds described above is their instability, especially in aqueous solutions, in which they easily undergo hydrolysis to 1-nitroacridone, a water-insoluble product, which makes impossible their storage for longer periods of time.

Moreover, the compounds show considerably high photosensitivity which deactivates them, as well as having high toxicity.

The 1-nitro-9-dialkylaminoisoalkylaminoacridines, or their salts of the present invention, are characterized by the formula 1, above, wherein R is lower alkyl, such as methyl, or ethyl, $R^1$ is a hydrogen atom or methyl, $R^2$ is the same as $R^1$, with the proviso that $R^1$ is not equal to $R^2$, and n = 0 or 2. A method for preparing the 1-nitro-9-dialkylaminoisoalkylaminoacridines, or their salts, of the formula 1, above, wherein R, $R^1$, $R^2$, and n are as defined above, comprises, according to the invention, in that (1-nitroacridyl-9)-pyridinium chloride, or its salt, is mixed with phenol, and is heated to a temperature of from 50° to 120° C. and, after cooling to a room temperature, the dialkylaminoisoalkylamine, or its salt, is added, and the whole mixture is heated again to a temperature from 50° to 120° C., and after cooling the reaction mixture is poured into an organic, non-polar, water-immiscible solvent, it is then made alkaline with an alkaline hydroxide; thereafter the 1-nitro-9-dialkylaminoisoalkylaminoacridine, obtained in the form of a base is dried and crystallized, and optionally, it is transformed into its salts of non-organic acids, such as hydrochlorides, hydrobromides, sulphates, or their salts of organic acids, such as lactates, citrates, succinates, or it is extracted with an organic, water-immiscible solvent and then dried, or, subsequently, it is acidified with an ether solution of hydrogen chloride and crystallized from a mixture of organic solvents.

Another method for preparing the 1-nitro-9-dialkylaminoisoalkylaminoacridines, or their salts, of the formula 1, above, wherein R, $R^1$, $R^2$, and n have the meaning given above, according to the invention, mixing 1-nitro-9-phenoxyacridine or its salt, with phenol and dialkylaminoisoalkylamine, or its salt and heating the mixture to a temperature of from 80° to 120° C, and then cooling the reaction mixture to room temperature, diluting it with an organic, water-immiscible solvent and making it alkaline with an aqueous solution of potassium carbonate; subsequently, the 1-nitro-9-dialkylaminoisoalkylaminoacridine obtained, in the form of a base, is extracted with an organic solvent, dried, and crystallized, and then, optionally, it is transformed into salts of non-organic acids, such as hydrochlorides, hydrobromides, sulphates, or into salts or organic acids, such as, lactates, succinates, citrates, or it is extracted with an organic solvent, dried, and may eventually be acidified with an ether solution of hydrogen chloride, and crystallized from an organic solvent.

The anti-neoplastic properties of the subject group of new derivatives of the 1-nitro-9-dialkylaminoisoalkylaminoacridines were investigated many times, using the tests described below:

I. Methods in vitro

1. Tissue culture (LS-leukocytic series lines)

The investigations were carried out using the tissue culture method elaborated by Eagle and Foley (Eagle H., Foley O. H., Cancer Research 18, 1017 (1958)), modified by Smith and collaborators (Smith G. G., Lummis W. L., Grady J. E., Cancer Research 19, 843–847 (1959)).

The experiments were carried out on neoplastic cells of human origin, so-called LS-lines (leukocytic series lines), using the Eagle's nutrient medium with 1% of calf's serum added. The tests were performed in test-tubes, inoculating them with 4 ml of a suspension (40–80 thousand cells), which is equivalent to 40–80 μg of cell protein. The growth of the culture was determined by means of an increase in cell protein. This determination was carried out in a photometric manner, using the Folin-Cicaltean's reagent according to the method elaborated by Oyama (Oyama V. J., Eagle H., Proc.Soc.Exp.Biol.Med. 91, 305 (1956) 25, (3/2), 522 (1965)).

Simultaneously with inoculation of test-tubes containing the cells, an amount of 0.2 ml of aqueous solution of the compound being tested was added, so that the concentrations were as follows:

100, 10, 1, 0.1, 0.01, and 0.001 μg/ml of the nutrient medium. The test-tubes were incubated at a temperature of 37° C. for 72 hours and the increase in cell protein was determined in these test-tubes, to which the preparation was added, as well as in the control test-tubes, too. Each concentration was determined by performing two tests at once. The solution concentrations of the substance, at which 50% growth inhibition was observed as compared to the control was also determined — the so-called $ID_{50}$. The percent of the inhibition was calculated according to the following formula:

$$\% \text{ inhibition} = \frac{\text{total amount LS in control} - \text{final amount of LS in the test}}{\text{total amount LS in control} - \text{initial amount of LS in control}}$$

According to the generally accepted norms, compounds considered to be active are those which have an $ID_{50} \leq 1$ μg/ml, and it is considered, that such compounds should undergo clinical investigations, without regard to the results obtained during the investigation in vivo. The compounds belonging to the group mentioned above, were tested by this method several times. The value $ID_{50}$ was 0.001 g/ml, correspondingly.

2. Method of Miyamura (cells of Ehrlich's cancer)

The method consists in a determination of activity inhibition of dehydrogenase activity in cells showing symptoms of Ehrlich's cancer ($5 \times 10^6$ in ml), by the compound tested, the measure of which is the diameter of the zone of non-reduced redox indicator (resazurine), which is formed around the cylinder containing 1% of a solution of the compound tested after 5 hours of incubation at a temperature of 37° C. According to commonly accepted criteria, the compounds, for which the inhibition zone is at least 20 mm, are accepted as active ones.

The derivatives of acridine, presented herein, show exceptionally high anti-neoplastic activity by this test, in the range of from 28 to 30 mm for individual compounds.

3. Inhibition of germination of cress seeds (growth test)

On a Petri dish 80 mm in diameter, are placed, as uniformly as possible, 20–25 cress seeds on two layers of filter-paper. Subsequently, on these dishes is poured 30 ml of solution of the compound to be tested, in a concentration of 1 mg/ml, whereas to the control distilled water was added. The dishes were incubated for 24 hours at a temperature of from 20°–30° C. and then the length of the germs was measured.

The effect of the inhibition is expressed in percent of the average length decrease of the germs tested, in comparison to the control ones.

The percent of germination inhibition of cress seeds for the applied group of compounds 86-88%.

II. Methods in vivo

The inhibition of growth of Crocker Sarcoma (Sa-180) in mice.

For these experiments mice, three months old and about 25 g in weight were used. Each of them was inoculated with a section of sarcoma (Sa-180 and then they were divided in groups: one of control — 10 mice, and two to four groups of the "being under treatment"-mice (7 mice each).

The compound investigated in corresponding doses were administered intraperitoneally in appropriate doses, prior to which a maximum tolerance dose was determined.

As a criterion for evaluation of the anti-neoplastic activity of the compounds investigated, the percent difference of the mean weights of tumours isolated from control mice, and the "treated" mice was used, taking into consideration the toxic effects. As active compounds were those which have inhibited, by at least 40%, the growth of the tumours, in at least two tests without any dying of the animals (less than 2 mice), or any mean losses of the weight greater than 4 g.

The investigations in vivo of several compounds were carried out several times, e.g., for the preparation labeled code number C-829, that is for 1-nitro-9-(2-dimethylamino-1-methylethylamino)-acridine dihydrochloride. Thirty-three (33) determinations were carried out in ten series using different doses, and an optimal inhibition of the growth of Crocker's sarcoma (Sa-180) was shown to be dependent upon the dose. In doses of 0.05 to 0.2 mg/kg the percent of inhibition was 17 to 73%, correspondingly.

The pharmacological examination showed, that from among the derivatives of acridine, this preparation was a compound of relatively lower toxicity. Its value $LD_{50}$ (i.v.) in mice and rats is, on average, 21 and 13 mg/kg, respectively. On the other hand, similar doses as related to oral administration are about 100 mg/kg.

The maximum tolerance doses (MTD) are lower by ca 20% in mice (i.v.), whereas in rats they are about 30% from a corresponding value $LD_{50}$.

The MTD-values by oral administration are even lower i.e., by 53–66% than the sharp lethal dose. The animals die over a prolonged period of time (up to 10 days), first of all with intensified symptoms of the alimentary canal, regardless of the way of administration. A sharp intestinal obstruction of the paralytic type occurs.

The preparation C-829 introduced intravenously, starting with doses increasing to 5 mg/kg (rabbits, cats), exerted a transient hypotension effect, which initially was not accompanied by any electrocardiographic changes. Higher doses, accompanied by intensified hypotension, induced some disturbances characteristic enough of the acridine compounds both in the atrio-ventricular and intraventricular conductivity. The perturbances consisted in prolonging the PQ section and in widening the QRS section. The lethal doses led to total auriculoventricular dissociation.

The preparation exerted a tonic action on the muscular coat of the blood-vessels and, probably, by the combination of the cellular action and of the toxic action on the stimulogenic-conductive system of the heart muscle (myocardium) may be due to a decreasing of the blood pressure observed. The circulatory effect following lower and moderate doses has a transient character.

The influence exerted by the preparation on the respiratory system is of two-phases. Initially, at the appearance of hypotension an instinctive respiratory excitation is noted; on the other hand, massive doses are depressive centrally for respiratory action, leading terminally to an apnoea.

The atropinism (atropinization) of animals (rabbits) does not change the action of the preparation on the circulatory system.

The action of the preparation C-829 on the smooth muscle is in the small intestine, and the urinary bladder in rabbit is spasmolytic (10 mg/kg), whereas in vitro it is rather a contracting (enterospasmatic) one on the muscular coat of the small intestine of both the guinea-pig and rat ($10^{-5}$ to $5 \times 10^{-5}$).

The preparation C-829 exerted an effect on the principal functions of the central nervous system. It was devoid, indeed, of an influence on the spontaneous motility of animals, however, in the interaction with soporific (hypnotic) drugs, it appeared to have a clear depressive component value, 10 $LD_{50}$. However, its action in the presence of cardiazol and strychnine was complex and non-characteristic.

In the sphere of influence of the preparation on reproductory functions, it should be noted, that the compound investigated was introduced over a period of 14 days, prior to the connexion of animals, only in dosages of 1/50 $LD_{50}$, reduced the amount of fructified females, as well as diminished the number of newborn animals in broods (casts). This was also accompanied by some retrograde microscopical metaplasia within the germinal epithelium of spermatic tubules of the testicles, leading to a disorder in the spermatogenesis. There was no observed pathological alteration in the ovary. There were also observed no macroscopic disorders of development of the foetus and newborn animals.

The extended toxicity studies were carried out for a three-month period in rabbits and rats. Doses of from 1/100 to 1/40 LD$_{50}$ were administered in the case of rabbits, and of from 1/150 to 1/50 LD$_{50}$ in the case of rats. It should be noted that the highest doses were also the maximum tolerance doses during 12 weeks.

The preparation C-829 did not change the picture of the peripheral blood in regard to both the leukocytic and erythrocytic levels, as well as to the hemoglobin level. However, it prolonged the blood clotting (coagulation) time, although it could not be correlated with the dosage introduced. The preliminary investigations did not show the influence of the preparation on the thrombocyte system, and probably the prothrombin system and the fibrinolytic systems were responsible for that.

In the lymphatic system, it was noted that there were very discretely marked involutional alterations, especially in the sphere of the mesenteric lymph nodes. The structure of the proliferous centers became imperceptible, and also the amount of small lymphocytes diminished. There was noted, using compensatory means, a hypertrophy of rete elements.

By prolonged exposition, the influence of the preparation C-829 on the functions of the parenchymateous organs (liver, kidneys) was investigated. It could not be determined, that it could influence the functions of the liver, when measured in blood serum by transaminase level (AlAt — Alamine aminotransferase) and by AspAt-Asparagine aminotransferase, as well as by the phosphatase level (both acidic and alkaline). Only the thymol turbidity test resulted as a positive one, using the highest dosage of the preparation. But it should be kept in mind, that this test is not too exact. The histological control showed that in the hepatic parenchyma appeared some weak (hardly perceptible) traits of the parenchymatous degeneration of glandular cells. These changes had a limited character and they did not appear in all animals.

The preparation C-829 neither induced any appearance of pathological components in urine, nor changed its specific weight. Also, the endogeneous creatinine level in the serum remained unchanged; the glomerular filterability was maintained within standard limits. In a part of animals tested, there were microscopically noted some focal parenchymatous degeneration character in renal tubules.

The preparation C-829, when administered as an aqueous solution, exerted a locally irritating action (0.05-1%), and when used in higher concentrations, even showed a narcotizing effect. It could be partially alleviated using, as solvent, the phosphate buffer solution of Sorensen at a pH 7.

An advantage of the derivatives, according to the invention, is their high anti-neoplastic activity, which was confirmed by many tests in vivo and in vitro, as well as a lower toxicity than the known acridine preparations, among them, in comparison with the preparation C-283 of the formula 2:

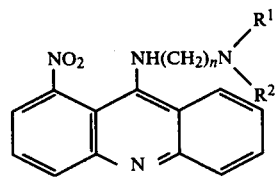

wherein R is (CH$_2$)$_n$, n is equal to 2 or 3, and R$^2$ is methyl or ethyl.

The 1-nitro-2-dialkylaminoisoalkylaminoacridines and a method for obtaining them, are illustrated by the following examples, given below:

Example I

To 6.8 of (1-nitroacryl-9)-pyridinium chloride 20 g of freshly distilled phenol is added, and the mixture is heated for 15 minutes in water bath at a temperature of 80° C. The mixture is then cooled, 4 g of the 1-methyl-2-dimethylaminoethylamine hydrochloride is added, and the mixture is heated again for 30 minutes at a temperature of 80° C. The reaction mixture is then cooled and about 20 ml of ether is added thereinto; subsequently, it is slowly poured into a cooled 10% solution of potassium hydroxide. Subsequently, the layers are separated, and the aqueous layer is extracted three times with ether. The ether extracts are combined, dried with anhydrous magnesium sulphate, the 1-nitro-9-(1-methyl-2-dimethylaminoethylamine)-acridine dihydrochloride is precipitated with an ether solution of hydrogen chloride which then is crystallized repeatedly from a mixture of dry methanol and ether. The orange-coloured crystals of 1-nitro-9-(1-methyl-2-dimethylaminoethylamine)acridine dihydrochloride of melting point about 220° C., with decomposition, are obtained.

Thin layer chromatography analysis (TLC) on:
1. silica gel DC in the solvent system: butanol: acetic acid: water — 4:1:5; R$_F$ = 0.2
2. neutral alumina (type E) in the system: benzene: ethyl acetate: ammonia — 15:59:1; — R$_F$ = 0.6

Elementary analysis for the formula: C$_{18}$H$_{22}$N$_4$O$_2$Cl$_2$: Calculated: C — 54.32%, H — 5.57%; N — 14.08%. Obtained: C — 53.86%, H — 5.87%; N — 13.89%.

Example II.

3.2 g of the 1-nitro-9-phenoxyacridine is dissolved in 15 ml of phenol and 1.2 g of the 2-methyl-2-dimethylaminoethylamine is added thereinto, then it is heated for 40 minutes at a temperature of 100° C. After heating, the reaction mixture is cooled, diluted with 30 ml of benzene and then poured into a 20% solution of potassium carbonate. The aqueous layer is separated and extracted twice with benzene. The benzene extract is dried with anhydrous sodium sulphate and, after distilling off a part of the solvent used, 1-nitro-9-(2-methyl-2-dimethylaminoacrylamino)-acridine of melting point 247° C. (with decomposition) is obtained which, subsequently, is acidified with an ether solution of hydrogen chloride to pH 4. The precipitated orange-coloured sediment is then crystallized twice from anhydrous ethanol. 1-Nitro-9-(2-methyl-2-dimethylaminoethylamino)acridine dihydrochloride of melting point 205° C., (with decomposition), is obtained. The yield is 72%.

Thin layer chromatography (TLC) on neutral alumina (type E) in the system: benzene: ethyl acetate: ammonia — 15:59:1; R$_F$ = 0.7.

Elementary analysis for the formula: C$_{18}$H$_{22}$N$_4$O$_2$Cl$_2$: Calculated: C — 54.32%; H — 5.57%; N — 14.08%. Obtained: C — 54.59%; H — 5.40%; N — 13.09%.

Example III.

3.4 g of the (1-nitroacridyl-9)-pyridinium chloride, 10 g of phenol and 2 g of the 1-methyl-4-dimethylaminobutylamine dihydrochloride are heated at a temperature of 100° C for 30 minutes. After cooling, the reaction mixture is made alkaline with a 10% aqueous solution of sodium hydroxide and is then extracted twice with benzene. The collected benzene extracts are dried with anhydrous sodium sulphate and, after filtering off the drying agent, it is acidified with an ether solution of hydrogen chloride. The orange-coloured precipitate of the 1-nitro-9-(1-methyl-4-dimethylaminobutylamine)-acridine dihydrochloride, obtained in this way, is then crystallized twice from a mixture of dry ethanol and acetone. The melting point of the compound obtained is 235° C. (with decomposition). Chromatographic analysis on neutral alumina (type E) in the system: benzene: ethyl acetate: ammonia — 15:59:1; $R_F = 0.55$.

Elementary analysis for the formula: $C_{20}H_{26}N_4O_2$: Calculated: C — 56.52%; H — 6.17%; N — 13.18%. Obtained: C — 56.38%; H — 6.12%; N — 13.03%.

Examples IV to VII.

Analogously, as in the Examples I to III, the following derivatives were obtained as shown in the table below:

TABLE

| Nr. of Example | Derivative nomenclature | Melting point | Method for obtaining them |
|---|---|---|---|
| IV | 1-nitro-9-(2-methyl-2-dimethylaminoethylamino)-acridine citrate | 185° with decomposition | II |
| V | 1-nitro-9-(2-methyl-2-dimethylaminoethylamino)-acridine tartrate | 172° C. | II |
| VI | 1-nitro-9-(2-methyl-2-dimethylaminoethylamino)-acridine methane sulphonate | 300° C. | II |
| VII | 1-nitro-9-(2-methyl-2-dimethylaminoethylamino)-acridine hydrobromide | 248° C. with decomposition | II |

We claim:

1. A compound selected from the group consisting of 1-nitro-9-dialkylaminoisoalkylaminoacridines, and their salts of the formula 1:

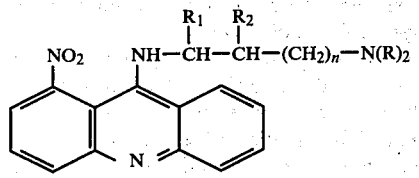

wherein R is methyl, $R^1$ is selected from the group consisting of a hydrogen atom and methyl, $R^2$ is the same as $R^1$, with the proviso that $R^1$ is not equal to $R^2$, and n = 0.

2. A compound according to claim 1 which is 1-nitro-9-(2-dimethylamino-1-methylethylamino)-acridine dihydrochloride.

* * * * *